(12) United States Patent
Kaneko et al.

(10) Patent No.: US 11,987,811 B2
(45) Date of Patent: *May 21, 2024

(54) METHOD FOR PRODUCING CD4-POSITIVE T CELLS FROM PLURIPOTENT STEM CELLS

(71) Applicant: Kyoto University, Kyoto (JP)

(72) Inventors: Shin Kaneko, Kyoto (JP); Norihiro Ueda, Kyoto (JP); Yasushi Uemura, Kashiwa (JP)

(73) Assignee: KYOTO UNIVERSITY, Kyoto (JP)

( * ) Notice: Subject to any disclaimer, the term of this patent is extended or adjusted under 35 U.S.C. 154(b) by 6 days.

This patent is subject to a terminal disclaimer.

(21) Appl. No.: 15/767,917

(22) PCT Filed: Oct. 14, 2016

(86) PCT No.: PCT/JP2016/080582
§ 371 (c)(1),
(2) Date: Apr. 12, 2018

(87) PCT Pub. No.: WO2017/065288
PCT Pub. Date: Apr. 20, 2017

(65) Prior Publication Data
US 2018/0298337 A1    Oct. 18, 2018

(30) Foreign Application Priority Data

Oct. 15, 2015   (JP) .................................. 2015-203482

(51) Int. Cl.
| | | |
|---|---|---|
| *C12N 5/0783* | (2010.01) | |
| *A61K 35/17* | (2015.01) | |
| *C12N 5/0735* | (2010.01) | |
| *C12N 15/86* | (2006.01) | |
| *A61K 39/00* | (2006.01) | |
| *A61P 35/02* | (2006.01) | |

(52) U.S. Cl.
CPC ............ *C12N 5/0637* (2013.01); *A61K 35/17* (2013.01); *C12N 5/0606* (2013.01); *C12N 15/86* (2013.01); *A61K 39/00* (2013.01); *A61P 35/02* (2018.01); *C12N 2500/30* (2013.01); *C12N 2501/125* (2013.01); *C12N 2501/165* (2013.01); *C12N 2501/26* (2013.01); *C12N 2502/11* (2013.01); *C12N 2502/1171* (2013.01); *C12N 2502/1323* (2013.01); *C12N 2506/45* (2013.01); *C12N 2510/00* (2013.01); *C12N 2740/10043* (2013.01); *C12N 2770/00043* (2013.01)

(58) Field of Classification Search
CPC .... C12N 5/0637; C12N 5/0606; C12N 15/86; C12N 2506/45; C12N 2502/1323; C12N 2502/1171; C12N 2510/00; C12N 2501/165; C12N 2501/125; C12N 2501/26; C12N 2740/10043; C12N 2500/30; C12N 2502/11; C12N 2770/00043; A61K 35/17; A61K 39/00; A61P 35/02; A61P 35/00

See application file for complete search history.

(56) References Cited

U.S. PATENT DOCUMENTS

| | | |
|---|---|---|
| 2010/0184214 A1 | 7/2010 | Inoue |
| 2011/0053267 A1 | 3/2011 | Nakauchi |
| 2012/0040458 A1 | 2/2012 | Yonemitsu |

FOREIGN PATENT DOCUMENTS

| | | |
|---|---|---|
| EP | 2 853 590 A1 | 4/2015 |
| JP | 2015-130881 A | 7/2015 |
| WO | WO 2008/143047 A1 | 11/2008 |
| WO | WO 2011/096482 A1 | 6/2013 |
| WO | WO 2013/176197 A1 | 11/2013 |

OTHER PUBLICATIONS

Sleckman et al., Nature, 328: 351-353, 1987.*
Wagner et al., Cancer Immunol Immunother (2003) 52: 89-96.*
Themeli et al., Nat Biotechnol. Oct. 2013; 31(10):1-20.*
Kim et al. Cell Stem Cell, 4(6): 472-476, 2009.*
Zhou et al., Cell Stem Cell, 4: 381-384, 2009.*
Ueda et al (3424 Generation of BCR-ABL Reactive CD4+ T Helper Cells By reprograming and redifferentiation, ASH 57th Annual Meeting & Exposition https://ash.confex.com/ash/2015/ebprogramscheduler/Paper78687.html, p. 1 (Year: 2015).*
Miro et al Journal of Immunology, 177: 3625-3634 (Year: 2006).*
Ballhausen et al J. Exp. Med. 167, 1493-1488 (Year: 1988).*
Kaneko et al Journal of the Japanese Society for Regenerative Medicine, 11 (4), pp. 379-382 abstract (Year: 2012).*
Ueda et al Proceedings of the Japanese Society for Immunology,, vol. 43, p. 167, 3-C-W40-4-P, abstract (Year: 2014).*
Ballhausen et al., "Acquisition of an additional antigen specificity after mouse CD4 gene transfer into a T helper hybridoma", *J. Exp. Med.*, vol. 167, No. 4, 1988, pp. 1493-1498.
Haque et al., "Programming of regulatory T cells from pluripotent stem cells and prevention of autoimmunity", *J. Immunol.*, vol. 189, No. 3, 2012, pp. 1228-1236.
Kaneko, Shin, "Reprogramming of antigen-specific CD4 T cells to regulatory T cells via T-iPS cells", *Journal of Japanese Society for Regenerative Medicine*, vol. 11, No. 4, 2012, pp. P63-P66.
Miro et al., "T Cell-Dependent Activation of Dendritic Cells Requires IL-12 and IFN-Signaling in T Cells", *J. Immunol.*, vol. 177, No. 6, 2006, pp. 3625-3634.

(Continued)

*Primary Examiner* — Anoop K Singh
(74) *Attorney, Agent, or Firm* — Knobbe, Martens, Olson & Bear, LLP (57) ABSTRACT

An object of the present invention is induction of CD4-positive T cells from pluripotent stem cells. This object is achieved by production of CD4-positive T cells by introducing a CD4 gene or a gene product thereof into T cells induced from pluripotent stem cells.

9 Claims, 4 Drawing Sheets
Specification includes a Sequence Listing.

(56) References Cited

OTHER PUBLICATIONS

Nishimura et al., "Generation of Rejuvenated Antigen-Specific T Cells by Reprogramming to Pluripotency and Redifferentiation", *Cell Stem Cell*, vol. 12, No. 1, 2013, pp. 114-126.

Ueda et al., "Generation of BCR-ABL reactive CD4 T lymphocytes by reprogramming and redifferentiation", *Proceedings of the Japanese Society for Immunology, Academic Meeting Record*, vol. 43, 2014, p. 167, 3-C-W40-4-P.

Ueda et al., "3424 Generation of BCR-ABL Reactive CD4+ T Helper Cells By Reprograming andRedifferentiation", ASH 57th Annual Meeting & Exposition, retrieved on Dec. 8, 2016 <http://ash.confex.com/ash/2015/webprogramscheduler/Paper78687.html>.

International Search Report for International Application No. PCT/JP2016/080582, dated Dec. 27, 2016, 4 pages.

Notification of Transmittal of Translation of the International Preliminary Report onPatentability for International Patent Application No. PCT/JP2016/080582, dated Apr. 26, 2018, 9 pages.

Office Action dated Sep. 29, 2020 received in Japanese Patent Application No. 2017-545495.

Doetschman et al., The in vitro development of blastocyst-derived embryonic stem cell lines: formation of visceral yolk sac, blood islands and myocardium, Journal of Embryology and Experimental Morphology, vol. 87, pp. 27-45, 1985.

Iriguchi et al., A clinically applicable and scalable method to regenerate T-cells from iPSCs for off-the-shelf T-cell immunotherapy, Nature Communications, vol. 12, No. 430, pp. 1-15, 2021.

Nishimura et al., Generation of Rejuvenated Antigen-Specific T Cells by Reprogramming to Pluripotency and Redifferentiation, Cell Stem Cell, vol. 12, pp. 114-126, 2013.

Ueda et al., Generation of TCR-Expressing Innate Lymphoid-like Helper Cells that Induce Cytotoxic T Cell-Mediated Anti-leukemic Cell Response, Stem Cell Reports, vol. 10, pp. 1935-1946, 2018.

Ueda et al., Non-clinical efficacy, safety and stable clinical cell processing of induced pluripotent stem cell-derived anti-glypican-3 chimeric antigen receptor-expressing natural killer/innate lymphoid cells, Cancer Science, vol. 00, pp. 1-13, 2020.

* cited by examiner

METHOD FOR PRODUCING CD4-POSITIVE T CELLS FROM PLURIPOTENT STEM CELLS

TECHNICAL FIELD

The present invention relates to a method for inducing CD4-positive T cells, which method comprises a step of introducing a CD4 gene or a gene product thereof into T cells induced from pluripotent stem cells.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 28021056_1.txt, the date of creation of the ASCII text file is Apr. 10, 2018, and the size of the ASCII text file is approximately 4 KB. The information in the electronic format of the Sequence Listing is incorporated herein by reference in its entirety.

BACKGROUND ART

Immune surveillance against tumors is established by cytotoxic T cells (CTLs), which are mainly composed of CD8-positive cells that directly injure tumors, and helper T cells (Th cells), which are mainly composed of CD4-positive cells and enhance the function of CTLs. On the other hand, dendritic cells (DCs) have a role as a control tower that controls the dynamics of other immune cells. Th cells are thought to be capable of producing an antitumor effect by activation of CTLs through activation of DCs.

If induction of tumor antigen-specific Th cells from pluripotent stem cells such as induced pluripotent stem (iPS) cells is possible, it may lead to development of a novel cellular immunotherapy based on administration of such cells into the living body for induction of a strong antitumor immune response. There has been a report on a method in which iPS cells are prepared from antigen-specific CD8-positive CTLs, followed by induction of the resulting cells to differentiate again into CD8-positive CTLs (Non-patent Document 1 and Patent Document 1). In this method, since T-cell receptors (TCRs) of the CD8-positive CTLs are consistently taken over, the CD8-positive CTLs induced from the iPS cells exhibit the same antigen specificity as that of the original cells.

T cell coreceptors (CD8 molecules in cases of CD8-positive CTLs, or CD4 in cases of CD4-positive Th cells) effectively enhance the signals input into the cells upon recognition of antigens by TCRs, and this results in effective induction of antigen-specific immune reactions of the T cells. However, preparation of cells expressing CD4 molecules is difficult by the method described in Non-patent Document 1 although the method allows induction of cells expressing CD8 molecules. Thus, in cells induced from iPS cells derived from CD4-positive Th cells, induction of sufficient helper function is impossible because of lack of CD4 molecules.

PRIOR ART DOCUMENTS

Patent Document

Patent Document 1: WO 2011/096482

Non-Patent Document

Non-patent Document 1: Nishimura T, et al., Cell Stem Cell. 12(1): 114-126, 2013

SUMMARY OF THE INVENTION

Problems to be Solved by the Invention

An object of the present invention is production of CD4-positive T cells from pluripotent stem cells. Another object of the present invention is activation of dendritic cells using CD4-positive T cells obtained by this method.

Means for Solving the Problems

In order to achieve the above objects, and in view of the fact that T cells induced from pluripotent stem cells by a conventional method lack expression of CD4, the present inventors introduced a CD4 gene into the T cells. As a result, the present inventors discovered that the resulting cells activate dendritic cells to the same extent as CD4-positive T cells isolated from the living body, thereby completed the present invention.

That is, the present invention provides the following inventions.

[1] A method for inducing CD4-positive T cells, the method comprising introducing a CD4 gene or a gene product thereof into T cells induced from pluripotent stem cells.

[2] The method according to [1], wherein said T cells have been induced from pluripotent stem cells by the method comprising:
(1) inducing CD34-positive hematopoietic progenitor cells from pluripotent stem cells; and
(2) culturing the CD34-positive hematopoietic progenitor cells obtained in the Step (1), in the presence of FLT3L (Flt3 Ligand) and IL (Interleukin)-7.

[3] The method according to [2], wherein said process further comprises the following Step (3):
(3) co-culturing the cells obtained in the Step (2), with peripheral blood mononuclear cells (PBMCs), in the presence of IL-7 and IL-15.

[4] The method according to [2] or [3], wherein said process further comprises bringing the cells obtained in the Step (2) into contact with mitogen and/or bringing the cells obtained in the Step (3) into contact with mitogen.

[5] The method according to any one of [2] to [4], wherein the Step (1) comprises co-culturing pluripotent stem cells with C3H10T1/2, followed by co-culturing with C3H10T1/2 in the presence of VEGF (Vascular Endothelial Growth Factor Receptor), FLT3L, and SCF (Stem Cell Factor).

[6] The method according to any one of [2] to [5], wherein the Step (2) comprises co-culturing the CD34-positive hematopoietic progenitor cells with stromal cells.

[7] The method according to [6], wherein the stromal cells are OP9 cells expressing Delta-1.

[8] The method according to any one of [1] to [7], wherein introduction of a CD4 gene or a gene product thereof is performed by introducing a CD4 gene with a retrovirus.

[9] The method according to any one of [1] to [8], wherein the pluripotent stem cells have a reconstituted TCR sequence(s) of interest.

[10] The method according to [9], wherein the pluripotent stem cells are human iPS cells induced from lymphocytes recognizing an antigen(s) of interest.

[11] The method according to [10], wherein the lymphocytes recognizing an antigen(s) of interest are lymphocytes recognizing BCR/ABL.

[12] A method for activating dendritic cells, comprising bringing CD4-positive T cells produced by the method according to any one of [1] to [11] into contact with isolated DCs in vitro in the presence of an antigen(s).

[13] The method according to [12], wherein the antigen is a BCR/ABL fragment.

[14] A cancer treating agent comprising a CD4-positive T cell produced by the method according to any one of [1] to [11].

[15] The cancer treating agent according to [14], further comprising an antigen.

[16] The cancer treating agent according to [15], wherein the antigen is a BCR/ABL fragment.

[17] A cancer treating agent comprising a dendritic cell activated by the method according to [12] or [13].

Effects of the Invention

According to the present invention, functional CD4-positive T cells can be produced by introducing a CD4 gene or a gene product thereof into T cells induced from pluripotent stem cells. Further, according to the present invention, dendritic cells can be activated using the CD4-positive T cells. Thus, according to the present invention, CD4-positive T cells can be produced from pluripotent stem cells, and a therapeutic agent for cancer which comprises CD4-positive T cells derived from pluripotent stem cells and activates the immune function can be provided.

EMBODIMENTS FOR CARRYING OUT THE INVENTION

The present invention provides a method for inducing CD4-positive T cells, the method comprising introducing a CD4 gene or a gene product thereof into T cells induced from pluripotent stem cells.

Pluripotent Stem Cells

In the present invention, the pluripotent stem cells are stem cells having pluripotency that allows differentiation into many kinds of cells present in a living body, which stem cells also have the growth ability. The pluripotent stem cells at least include arbitrary cells which can be induced into the hematopoietic progenitor cells to be used in the present invention. Examples of the pluripotent stem cells include, but are not limited to, embryonic stem (ES) cells, embryonic stem cells derived from a cloned embryo obtained by nuclear transfer (ntES cells), germline stem cells ("GS cells"), embryonic germ cells ("EG cells"), induced pluripotent stem (iPS) cells, and pluripotent cells derived from cultured fibroblasts or bone marrow stem cells (Muse cells).

Methods for producing iPS cells are known in the art. These cells can be produced by introducing reprogramming factors into arbitrary somatic cells. Examples of the reprogramming factors herein include genes such as Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3, and Glis1, and gene products thereof. These reprogramming factors may be used individually, or any of these may be used in combination. Examples of the combinations of the reprogramming factors include those described in WO 2007/069666; WO 2008/118820; WO 2009/007852; WO 2009/032194; WO 2009/058413; WO 2009/057831; WO 2009/075119; WO 2009/079007; WO 2009/091659; WO 2009/101084; WO 2009/101407; WO 2009/102983; WO 2009/114949; WO 2009/117439; WO 2009/126250; WO 2009/126251; WO 2009/126655; WO 2009/157593; WO 2010/009015; WO 2010/033906; WO 2010/033920; WO 2010/042800; WO 2010/050626; WO 2010/056831; WO 2010/068955; WO 2010/098419; WO 2010/102267; WO 2010/111409; WO 2010/111422; WO 2010/115050; WO 2010/124290; WO 2010/147395; WO 2010/147612; Huangfu D, et al. (2008), Nat. Biotechnol., 26: 795-797; Shi Y, et al. (2008), Cell Stem Cell, 2: 525-528; Eminli S, et al. (2008), Stem Cells. 26:2467-2474; Huangfu D, et al. (2008), Nat. Biotechnol. 26:1269-1275; Shi Y, et al. (2008), Cell Stem Cell, 3, 568-574; Zhao Y, et al. (2008), Cell Stem Cell, 3:475-479; Marson A, (2008), Cell Stem Cell, 3, 132-135; Feng B, et al. (2009), Nat. Cell Biol. 11:197-203; R. L. Judson et al., (2009), Nat. Biotechnol., 27:459-461; Lyssiotis C A, et al. (2009), Proc Natl Acad Sci USA. 106:8912-8917; Kim J B, et al. (2009), Nature. 461:649-643; Ichida J K, et al. (2009), Cell Stem Cell. 5:491-503; Heng J C, et al. (2010), Cell Stem Cell. 6:167-74; Han J, et al. (2010), Nature. 463:1096-100; Mali P, et al. (2010), Stem Cells. 28:713-720; and Maekawa M, et al. (2011), Nature. 474: 225-9.

Examples of the somatic cells include, but are not limited to, any of fetal somatic cells, neonatal somatic cells, and mature, healthy or diseased somatic cells, as well as any of primary cultured cells, subcultured cells, and established cell lines. Specific examples of the somatic cells include (1) tissue stem cells (somatic stem cells) such as neural stem cells, hematopoietic stem cells, mesenchymal stem cells, and dental pulp stem cells; (2) tissue progenitor cells; and (3) differentiated cells such as blood cells (peripheral blood cells, cord blood cells, and the like), lymphocytes, epithelial cells, endothelial cells, muscle cells, fibroblasts (skin cells and the like), hair cells, hepatic cells, gastric mucosal cells, enterocytes, spleen cells, pancreatic cells (pancreatic exocrine cells and the like), brain cells, lung cells, kidney cells, and adipocytes.

In the present invention, for use in the purpose of production of CD4-positive T cells, iPS cells are preferably produced using, as somatic cells, lymphocytes (preferably T cells) that have undergone gene rearrangement of T cell receptor (TCR). In the present invention, in cases where lymphocytes are used, the reprogramming step is preferably carried out after activation of the lymphocytes by stimulation with an anti-CD3 antibody and an anti-CD28 antibody, or by stimulation with an antigen peptide(s) of interest, in the presence of interleukin-2 (IL-2). Such stimulation can be carried out by, for example, culturing the lymphocytes for a predetermined period in a medium supplemented with IL-2, the anti-CD3 antibody, and the anti-CD28 antibody. The anti-CD3 antibody and the anti-CD28 antibody may be those to which magnetic beads or the like are bound. Instead of adding these antibodies to the medium, the T cells may be stimulated by culturing for a certain period of time on a culture dish having a surface to which the anti-CD3 antibody and the anti-CD28 antibody are bound. The stimulation may also be carried out by adding an antigen peptide(s) that can be recognized by human T cells to the medium. The antigen peptide means a peptide having a sequence of not less than nine amino acids constituting an antigen protein of interest. Examples of such a peptide include peptides having a sequence composed of not less than 9 amino acids constituting the b3a2 subtype (which is also simply referred to as b3a2) of the p210 BCR/ABL chimeric gene. Thus, by culturing lymphocytes in a medium supplemented with an antigen peptide, lymphocytes that recognize the antigen peptide can be selectively grown.

The CD4-positive T cells produced in the present invention preferably has a desired antigen specificity. Thus, the lymphocytes to be used as the origin of the iPS cells preferably have a desired antigen specificity, and the lymphocytes may be specifically isolated by purification using an affinity column or the like to which the antigen of interest is immobilized. In this purification, a method in which lymphocytes having a desired antigen specificity are purified from a human tissue using a tetramer of MHC (major histocompatibility complex) (the so-called "MHC tetramer") to which an antigen of interest is bound may also be employed.

In the present invention, the mammalian individual from which the somatic cells are collected is not limited. The mammalian individual is preferably human. In cases where CD4-positive T cells prepared by the method of the present invention are used for blood transfusion, the somatic cells to be used as the origin of the iPS cells are preferably isolated from the subject for which the blood transfusion of the CD4-positive T cells is to be carried out, from the viewpoint of easily matching the type of the human leukocyte antigen (HLA) with that of the patient for which the blood transfusion is to be carried out.

Method for Induction of T Cells from Pluripotent Stem Cells

The method for induction of T cells from pluripotent stem cells may be carried out by a known method. Examples of the method include a method comprising the following Steps (1) to (3):

(Step 1) inducing CD34-positive hematopoietic progenitor cells from pluripotent stem cells;

(Step 2) culturing the CD34-positive hematopoietic progenitor cells obtained in the Step (1), in the presence of FLT3L and IL-7; and (Step 3) co-culturing the cells obtained in the Step (2) with peripheral blood mononuclear cells in the presence of IL-7 and IL-15.

In the present invention, the T cell means a cell having TCRs on the cell surface. For example, the cell may also have CD4 and CD8 on the cell surface. Thus, in the present invention, from the viewpoint of induction of T cells, the Step (1) and the Step (2) may be included. For the purpose of efficiently increasing the content of T cells, the Step (3) is preferably further included.

In the present invention, the induction of T cells means production of T cells as a cell population that may also contain other cell species. For example, it may be production of a cell population containing T cells at the ratio of not less than 60%, not less than 70%, not less than 80%, not less than 90%, or not less than 95%.

(Step 1) Step of Inducing Hematopoietic Progenitor Cells from Pluripotent Stem Cells In the present invention, hematopoietic progenitor cells are cells that are capable of differentiation into blood cells such as lymphocytes, eosinophils, neutrophils, basophils, erythrocytes, and megakaryocytes. In the present invention, hematopoietic progenitor cells and hematopoietic stem cells are not distinguished from each other, and regarded as the same kind of cells unless otherwise specified. Accordingly, in the present invention, hematopoietic progenitor cells include hematopoietic stem cells. The hematopoietic progenitor cells can be recognized based on, for example, the positivity of CD34, or the positivity of CD34 and CD43, which are surface antigens.

In a method for inducing hematopoietic progenitor cells from pluripotent stem cells, the hematopoietic progenitor cells can be prepared from a net-like structure (which is also referred to as ES-sac or iPS-sac) obtained by co-culturing pluripotent stem cells with C3H10T1/2, and then co-culturing them with C3H10T1/2 in the presence of VEGF, FLT3L, and SCF. In this process, the culture may be carried out with addition of vitamin C. The "net-like structure" herein is a three-dimensional sac-shaped structure (having a space in the inside) derived from pluripotent stem cells. The structure is formed with an endothelial cell population and/or the like, and contains hematopoietic progenitor cells in the inside. Alternatively, hematopoietic progenitor cells can be prepared from a net-like structure obtained by culturing pluripotent stem cells in the presence of VEGF on C3H10T1/2 according to a method described in Takayama N., et al. J Exp Med. 2817-2830 (2010). Other examples of methods for producing hematopoietic progenitor cells from pluripotent stem cells include a method based on formation of embryoid bodies and addition of cytokines (Chadwick et al. Blood 2003, 102: 906-15; Vijayaragavan et al. Cell Stem Cell 2009, 4: 248-62; Saeki et al. Stem Cells 2009, 27: 59-67), a method based on co-culture with stromal cells derived from a different species (Niwa A et al. J Cell Physiol. 2009 November; 221(2): 367-77), and a method based on combination of addition of cytokines and a coating agent (Matrigel or laminin fragment) (WO 2011/115308).

(Step 2) Step of Culturing Hematopoietic Progenitor Cells in Presence of FLT3L and IL-7

The medium to be used in the Step 2 is not limited, and may be prepared by using, as a basal medium, a medium used for animal cell culture, and adding FLT3L and IL-7 thereto. Examples of the basal medium include Iscove's Modified Dulbecco's Medium (IMDM), Medium 199, Eagle's Minimum Essential Medium (EMEM), αMEM medium, Dulbecco's modified Eagle's Medium (DMEM), Ham's F12 medium, RPMI 1640 medium, Fischer's medium, and Neurobasal Medium (Life Technologies), and mixed media of any of these. The medium may contain serum, or may be serum-free. If necessary, the basal medium may also contain one or more of substances such as albumin, insulin, transferrin, selenium, fatty acid, trace elements, 2-mercaptoethanol, thiol glycerol, lipids, amino acids, L-glutamine, non-essential amino acids, vitamins, growth factors, low molecular weight compounds, antibiotics, antioxidants, pyruvic acid, buffers, inorganic salts, and cytokines. Preferred examples of the basal medium in the Step 2 include αMEM medium supplemented with serum, L-glutamine, transferrin, and selenium.

The IL-7 concentration in the medium to be used in the Step 2 is usually 0.1 ng/ml to 50 ng/ml, for example, 0.1 ng/ml, 0.2 ng/ml, 0.3 ng/ml, 0.4 ng/ml, 0.5 ng/ml, 0.6 ng/ml, 0.7 ng/ml, 0.8 ng/ml, 0.9 ng/ml, 1 ng/ml, 2 ng/ml, 3 ng/ml, 4 ng/ml, 5 ng/ml, 10 ng/ml, 20 ng/ml, 30 ng/ml, 40 ng/ml, or 50 ng/ml. The concentration is preferably 1 ng/ml.

The FLT3L concentration in the medium to be used in the Step 2 is usually 1 ng/ml to 100 ng/ml, for example, 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 20 ng/ml, 50 ng/ml, or 100 ng/ml. The concentration is preferably 10 ng/ml.

An additive containing vitamin C, SCF, and TPO (thrombopoietin) may be further added to the medium to be used in the Step 2.

In the present invention, "vitamin C" means L-ascorbic acid and derivatives thereof, and "L-ascorbic acid derivative" means derivatives that become vitamin C by enzymatic reaction in the living body. Examples of the derivatives of L-ascorbic acid include vitamin C phosphate, ascorbic acid glucoside, ascorbyl ethyl, vitamin C ester, ascorbyl tetrahexyldecanoate, ascorbyl stearate, and ascorbyl 2-phosphate 6-palmitate. The vitamin C is preferably vitamin C phosphate. Examples of the vitamin C phosphate include L-ascorbic acid phosphate Na and L-ascorbic acid phosphate Mg.

In the present invention, the vitamin C is preferably added separately every four days, every three days, every two days, or every day during the culture period. The vitamin C is more preferably added every day. The addition of the vitamin C to the medium is carried out usually in an amount corresponding to 5 ng/ml to 500 ng/ml. The amount is preferably an amount corresponding to 5 ng/ml, 10 ng/ml, 25 ng/ml, 50 ng/ml, 100 ng/ml, 200 ng/ml, 300 ng/ml, 400 ng/ml, or 500 ng/ml.

The concentration of the SCF to be used for the production of the hematopoietic progenitor cells in the medium in the present invention is 10 ng/ml to 100 ng/ml, for example, 10 ng/ml, 20 ng/ml, 30 ng/ml, 40 ng/ml, 50 ng/ml, 60 ng/ml, 70 ng/ml, 80 ng/ml, 90 ng/ml, 100 ng/ml, 150 ng/ml, 200 ng/ml, or 500 ng/ml.

The concentration of the TPO to be used for the production of the hematopoietic progenitor cells in the medium in the present invention is 10 ng/ml to 100 ng/ml, for example, 10 ng/ml, 20 ng/ml, 30 ng/ml, 40 ng/ml, 50 ng/ml, 60 ng/ml, 70 ng/ml, 80 ng/ml, 90 ng/ml, 100 ng/ml, 150 ng/ml, 200 ng/ml, or 500 ng/ml.

In the Step 2, the hematopoietic progenitor cells may be cultured by adherent culture or suspension culture. In cases of adherent culture, a coated culture vessel may be used, and/or the hematopoietic progenitor cells may be co-cultured with feeder cells and/or the like. The feeder cells for the co-culture are preferably stromal cells. Specific examples of the stromal cells include a bone-marrow stromal cell line OP9 cells (available from Riken BioResource Center). The OP9 cells may be preferably OP9-DL1 cells, which constantly express Delta-like 1 (Dll1) (Holmes R1 and Zuniga-Pflucker J C. Cold Spring Harb Protoc. 2009(2)). In the present invention, in cases where OP9 cells are used as the feeder cells, Dll1, or a fusion protein of Dll1 and Fc or the like, may be separately provided and added to the medium as appropriate. In the present invention, examples of the Dll1 include proteins encoded by a gene having the nucleotide sequence of the NCBI accession number NM_005618 in cases of human, or NCBI accession number NM_007865 in cases of mouse; and naturally occurring mutants having a high sequence identity (for example, having a sequence identity of not less than 90%) to these proteins and having an equivalent function. The feeder cells are preferably replaced as appropriate during the culture. The replacement of the feeder cells may be carried out by transferring the subject cells that are being cultured onto feeder cells that are preliminarily plated. The replacement may be carried out every five days, every four days, every three days, or every two days.

In cases where suspension culture is carried out in the Step 2, the cells are preferably cultured while being allowed to form aggregates (also referred to as spheres) in a state where the cells are not adhering to the culture vessel. The culture may be, but not limited to, carried out using a culture vessel that has not been artificially treated for the purpose of enhancing adhesiveness to cells (for example, by coating treatment with an extracellular matrix or the like), or a culture vessel that has been subjected to coating treatment for artificially suppressing adhesion (for example, treatment with a polyhydroxyethylmethacrylate (poly-HEMA), a non-ionic surfactant polyol (e.g., Pluronic F-127), or a phospholipid analogue (e.g., a water-soluble polymer containing 2-methacryloyloxyethyl phosphorylcholine as a constituent (Lipidure)). In cases where suspension culture is carried out in the Step 2, the culture may be carried out with reference to Huijskens M J et al. (J Leukoc Biol. 96: 1165-1175, 2014).

In cases where adherent culture is carried out in the Step 2, the culture may be carried out using a culture vessel coated with an extracellular matrix. The coating treatment may be carried out by placing a solution containing the extracellular matrix in the culture vessel, and then removing the solution as appropriate. The extracellular matrix herein is a supramolecular structure present outside the cell, and may be either a naturally-occurring substance or an artificial (recombinant) substance. Examples of the extracellular matrix include substances such as polylysine, polyornithine, collagen, proteoglycan, fibronectin, hyaluronic acid, tenascin, entactin, elastin, fibrillin, and laminin, and fragments thereof. Any of these extracellular matrices may be used in combination. For example, the extracellular matrix may be a product prepared from cells, such as BD Matrigel (trademark).

The temperature conditions for the culture of the hematopoietic progenitor cells in the Step 2 are not limited. The temperature is, for example, about 37° C. to about 42° C., preferably about 37 to about 39° C. The culture period can be appropriately selected by those skilled in the art by monitoring of the number of cells and/or the like. Examples of the number of days include, but are not limited to, at least not less than 10 days, not less than 12 days, not less than 14 days, not less than 16 days, not less than 18 days, not less than 20 days, and not less than 21 days. The number of days is preferably 14 days.

The cells obtained in the Step 2 may be stimulated with mitogen. The mitogen in the present invention means a substance that promotes cell division of T cells, and examples of such a substance include pokeweed mitogen, anti-CD3 antibody, anti-CD28 antibody, phytohemagglutinin (PHA), concanavalin A (ConA), super antigens, and phorbol esters (including phorbol-12-myristate-13-acetate (PMA)).

(Step 3) Step of Co-Culturing with Peripheral Blood Mononuclear Cells in the Presence of IL-7 and IL-15

The Step 3 is a step of isolating the cells obtained in the Step 2 and co-culturing the cells with peripheral blood mononuclear cells.

The peripheral blood mononuclear cells to be used in the Step 3 are preferably allogeneic to the pluripotent stem cells used in Step 1. Accordingly, in cases where human pluripotent stem cells are used, the peripheral blood mononuclear cells are preferably human peripheral blood mononuclear cells. The peripheral blood mononuclear cells are preferably subjected to a treatment for prevention of self-proliferation. Examples of such a treatment include radiation irradiation and mitomycin treatment.

The medium to be used in the Step 3 is not limited, and may be prepared by using, as a basal medium, a medium used for animal cell culture, and adding IL-7 and IL-15 thereto. Examples of the basal medium include Iscove's Modified Dulbecco's Medium (IMDM), Medium 199, Eagle's Minimum Essential Medium (EMEM), αMEM medium, Dulbecco's modified Eagle's Medium (DMEM), Ham's F12 medium, RPMI 1640 medium, Fischer's medium, and Neurobasal Medium (Life Technologies), and mixed media of any of these. The medium may contain serum, or may be serum-free. If necessary, the basal medium may also contain one or more of substances such as albumin, insulin, transferrin, selenium, fatty acid, trace elements, 2-mercaptoethanol, thiol glycerol, lipids, amino acids, L-glutamine, non-essential amino acids, vitamins, growth factors, low molecular weight compounds, antibiotics, antioxidants, pyruvic acid, buffers, inorganic salts, and cytokines. Preferred examples of the basal medium in the Step 2 include RPMI 1640 medium supplemented with serum and L-glutamine.

The IL-7 concentration in the medium to be used in the Step 3 is 1 ng/ml to 100 ng/ml, for example, 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 20 ng/ml, 50 ng/ml, or 100 ng/ml. The concentration is preferably 10 ng/ml.

The IL-15 concentration in the medium to be used in the Step 3 is 1 ng/ml to 100 ng/ml, for example, 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 20 ng/ml, 50 ng/ml, or 100 ng/ml. The concentration is preferably 10 ng/ml.

For the purpose of promoting the cell division of the T cells, mitogen may be further added for preparation of the medium. As the mitogen, those described above may be used.

The culture temperature conditions in the Step 3 are not limited. The temperature is, for example, about 37° C. to about 42° C., preferably about 37 to about 39° C. The culture period can be appropriately selected by those skilled in the art by monitoring of the number of cells and/or the like. Examples of the number of days include, but are not limited to, at least not less than 10 days, not less than 12 days, not less than 14 days, not less than 16 days, not less than 18 days, not less than 20 days, and not less than 21 days. The number of days is preferably 14 days.

Method for Introducing CD4 Gene or Gene Product

The method for introducing the CD4 gene or gene product into the T cells is not limited, and examples of the method include the following methods. In the present invention, examples of the gene product include RNAs and proteins. The CD4 gene is preferably a human gene, and examples of the gene include those encoding a protein which has the amino acid sequence of GenBank Accession No. AAH25782 (SEQ ID NO:3) or an amino acid sequence having an identity of not less than 80%, preferably not less than 90%, more preferably not less than 95% thereto, which protein is capable of activating dendritic cells when it is introduced into T cells.

In cases where the CD4 is introduced in the form of a gene (DNA), it may be introduced into pluripotent stem cells by introduction of a vector such as a virus, plasmid, or artificial chromosome vector using a method such as lipofection, liposome, or microinjection. Examples of the virus vector include retrovirus vectors, lentivirus vectors, adenovirus vectors, adeno-associated virus vectors, and Sendai virus vectors. Examples of the artificial chromosome vector include human artificial chromosomes (HACs), yeast artificial chromosomes (YACs), and bacterial artificial chromosomes (BACs and PACs). Examples of the plasmid which may be used include plasmids for mammalian cells. The vector may contain a regulatory sequence such as a promoter, enhancer, ribosome binding sequence, terminator, or polyadenylation site for allowing expression of the CD4 gene; and, if necessary, a sequence of a selection marker such as a drug resistance gene (e.g., kanamycin resistance gene, ampicillin resistance gene, or puromycin resistance gene), thymidine kinase gene, or diphtheria toxin gene; a gene sequence of a reporter such as a fluorescent protein, β-glucuronidase (GUS), or FLAG; or the like. Examples of the promoter include the SV40 promoter, LTR promoter, CMV (cytomegalovirus) promoter, RSV (Rous sarcoma virus) promoter, MoMuLV (Moloney mouse leukemia virus) LTR, HSV-TK (herpes simplex virus thymidine kinase) promoter, EF-α promoter, CAG promoter, and TRE promoter (CMV minimal promoter having a Tet-responsive sequence containing seven consecutive tetO sequences). In cases where a TRE promoter is used, it is preferred to allow simultaneous expression of a fusion protein of tetR and VP16AD, or a fusion protein of reverse tetR (rtetR) and VP16AD in the same cells. Here, a vector having a TRE promoter and capable of expressing a fusion protein of reverse tetR (rtetR) and VP16AD is referred to as a drug-responsive induction vector. For incorporating an expression cassette composed of a promoter and a CD4 gene linked thereto into a chromosome of a pluripotent cell, and excising the expression cassette when necessary, the vector may have transposon sequences before and after this expression cassette. Examples of the transposon sequences include, but are not limited to, piggyBac. In another embodiment, for the purpose of removing the expression cassette, LoxP sequences may be placed before and after the expression cassette.

In cases where a drug-responsive induction vector is used, the CD4 gene may be introduced into the pluripotent stem cells, and the CD4 gene can be expressed by addition of the corresponding drug to the medium. Thus, in cases where the drug-responsive induction vector is used, the addition of the corresponding drug to the medium can be regarded as introduction of the CD4 gene. Examples of the corresponding drug include doxycycline. In cases where a vector having LoxP sequences are used, for example, the expression may be stopped by introduction of Cre into the cells after a predetermined period of time.

In cases where the CD4 is introduced in the form of an RNA, it may be introduced into the pluripotent stem cells by a method such as electroporation, lipofection, or microinjection.

In cases where the CD4 is introduced in the form of a protein, it may be introduced into the pluripotent stem cells by a method such as lipofection, fusion with a cell membrane-permeable peptide (e.g., HIV-derived TAT or polyarginine), or microinjection.

In cases where the CD4 is introduced in the form of such a gene product, since the half-life of the gene product is short, the introduction may be carried out a plurality of times. The number of times of the introduction may be calculated as appropriate taking into account the period during which expression of the CD4 gene is required, and referring to the half-life. Examples of the number of times of the introduction include three times, four times, five times, six times, and a larger number of times.

Method for Activating Dendritic Cells

The present invention provides a method for activating dendritic cells, comprising bringing the CD4-positive T cells produced by the above-described method into contact with dendritic cells in vitro in the presence of an antigen(s).

In the present invention, the dendritic cells are cells having a function by which an antigen can be incorporated and bound to an MHC molecule for presentation of the antigen. Since the dendritic cells can be activated by contacting with CD4-positive T cells produced by the method of the present invention, the dendritic cells may be immature dendritic cells.

The activation of dendritic cells means acquisition of a function by which antigen-specific T cells can be activated, more preferably means acquisition of a function by which antigen-specific CD8-positive T cells can be activated. The activation can also be carried out by confirmation of expression of CD83 or CMRF-44. The activation of dendritic cells is, in other words, maturation of immature dendritic cells into mature dendritic cells.

Preferably, the dendritic cells to be used in the present invention are dendritic cells isolated from a donor by a blood component separator and density gradient centrifugation, and have the same MHC molecules as those of CD4-positive T cells.

The antigen to be used in the activation of the dendritic cells in the present invention is a peptide having a sequence of at least nine consecutive amino acids in a protein specifically recognized by CD4-positive T cells produced by the method of the present invention. For example, in cases where the CD4-positive T cells have TCRs that specifically recognize the b3a2 peptide, the b3a2 peptide is used as the antigen.

The b3a2 peptide is a part of the protein encoded by the b3a2-type BCR/ABL chimeric gene, and has a sequence of at least nine consecutive amino acids. The b3a2-type BCR/ABL chimeric gene means a fusion gene of BCR and ABL, containing the B3 exon from the M-BCR portion of BCR, and the A2 exon from ABL.

The medium to be used for the activation of the dendritic cells may be a medium to be used for animal cell culture. Examples of the basal medium include Iscove's Modified Dulbecco's Medium (IMDM), Medium 199, Eagle's Minimum Essential Medium (EMEM), αMEM medium, Dulbecco's modified Eagle's Medium (DMEM), Ham's F12 medium, RPMI 1640 medium, Fischer's medium, and Neurobasal Medium (Life Technologies), and mixed media of any of these. The medium may contain serum, or may be serum-free. If necessary, the basal medium may also contain one or more of substances such as albumin, insulin, transferrin, selenium, fatty acid, trace elements, 2-mercaptoethanol, thiol glycerol, lipids, amino acids, L-glutamine, non-essential amino acids, vitamins, growth factors, low molecular weight compounds, antibiotics, antioxidants, pyruvic acid, buffers, inorganic salts, and cytokines.

The basal medium in the present invention is preferably RPMI 1640 medium supplemented with serum and L-glutamine.

The length of time required for the activation of the dendritic cells is not limited, and may be several hours. Examples of the length of time include 2 hours, 3 hours, 4 hours, 5 hours, and 6 hours. The length of time is preferably 5 hours.

Cancer Treating Agent

The present invention provides a cancer treating agent comprising CD4-positive T cells produced by the method described above, and/or containing dendritic cells activated by the method described above.

In cases where the treating agent comprises the CD4-positive T cells, the cancer to be treated is preferably cancer cells expressing an antigen specifically recognized by the CD4-positive T cells. For example, in cases where the CD4-positive T cells have TCRs that specifically recognize b3a2, the cancer to be treated is cancer cells expressing b3a2, that is, leukemia caused by a chromosome having a BCR/ABL chimeric gene (Philadelphia chromosome).

The dendritic cells activated by the CD4-positive T cells are also capable of activating lymphocytes (for example, CD8-positive T cells) that recognize an antigen other than the antigen recognized by the CD4-positive T cells, when the other antigen is presented. Thus, the cancer to be treated by the cancer treating agent containing dendritic cells is not limited.

In cases where the treating agent contains dendritic cells, the activated dendritic cells may be used as they are as the therapeutic agent. In cancer treatment, dendritic cells may be made to present a tumor antigen by methods such as mixing with a cell lysate of cancer cells, contacting with a peptide, or introduction of a tumor antigen gene, to provide the antigen-presenting dendritic cells as the cancer treating agent.

Examples of the method for administration of the cancer treating agent to a patient include a method in which the produced CD4-positive T cells, and/or the dendritic cells activated by the method described above, are suspended in physiological saline or the like, and the resulting suspension is directly transplanted to a muscle tissue of the patient, and a method in which the dendritic cells are suspended in physiological saline or the like, and the resulting suspension is intravenously injected.

EXAMPLES

The present invention is described below more specifically by referring to Examples. However, the scope of the present invention is not limited to these Examples.

iPS cells (b3a2-iPSC line) were established from isolated human b3a2-Th cells by the method described in Nishimura T, et al. (Cell Stem Cell. 12(1): 114-126, 2013). More specifically, isolated human b3a2-Th cells were cultured for 2 days in RPMI 1640+10% FBS+PSG (penicillin, streptomycin, and L-glutamine) supplemented with 20 ng/ml hIL-2, and gene transfer of OCT4, SOX2, KLF4, and c-MYC was carried out using a Sendai virus vector. After carrying out the gene transfer operation for two continuous days, 1×10⁵ cells were plated on irradiated MEFs (mouse embryonic fibroblasts), and a half amount of the medium was replaced with an iPS medium (Dulbecco's modified Eagle's medium/F12 medium supplemented with Knockout Serum Replacement, L-glutamine, non-essential amino acids, 2-mercaptoethanol, b-FGF, etc. this medium is available from, for example, ReproCELL) every day, thereby achieving complete replacement of the T cell medium with the iPS medium on Day 4 after the plating. In terms of the human b3a2-Th cells, human peripheral blood was collected with an informed consent, and peripheral blood mononuclear cells (PBMCs) were separated therefrom by density gradient centrifugation using Ficoll. The cells were then subjected to antigen stimulation with the b3a2 peptide (SEQ ID NO:1; ATGFKQSSKALQRPVAS) once every week, a total of three times, thereby allowing the growth of b3a2-Th cells. From the resulting cells, a b3a2-Th cell clone was obtained by limiting dilution.

In order to confirm that the established iPS cells were derived from b3a2-Th cells, reconstitution of the TCR gene was confirmed by the method described in Nishimura T, et al., Cell Stem Cell. 12(1):114-126, 2013.

C3H10T1/2 cells, and OP9 cells expressing Delta-like 1 (OP9-DL1 cells) were obtained from Riken BioResource Center.

Figure 1:
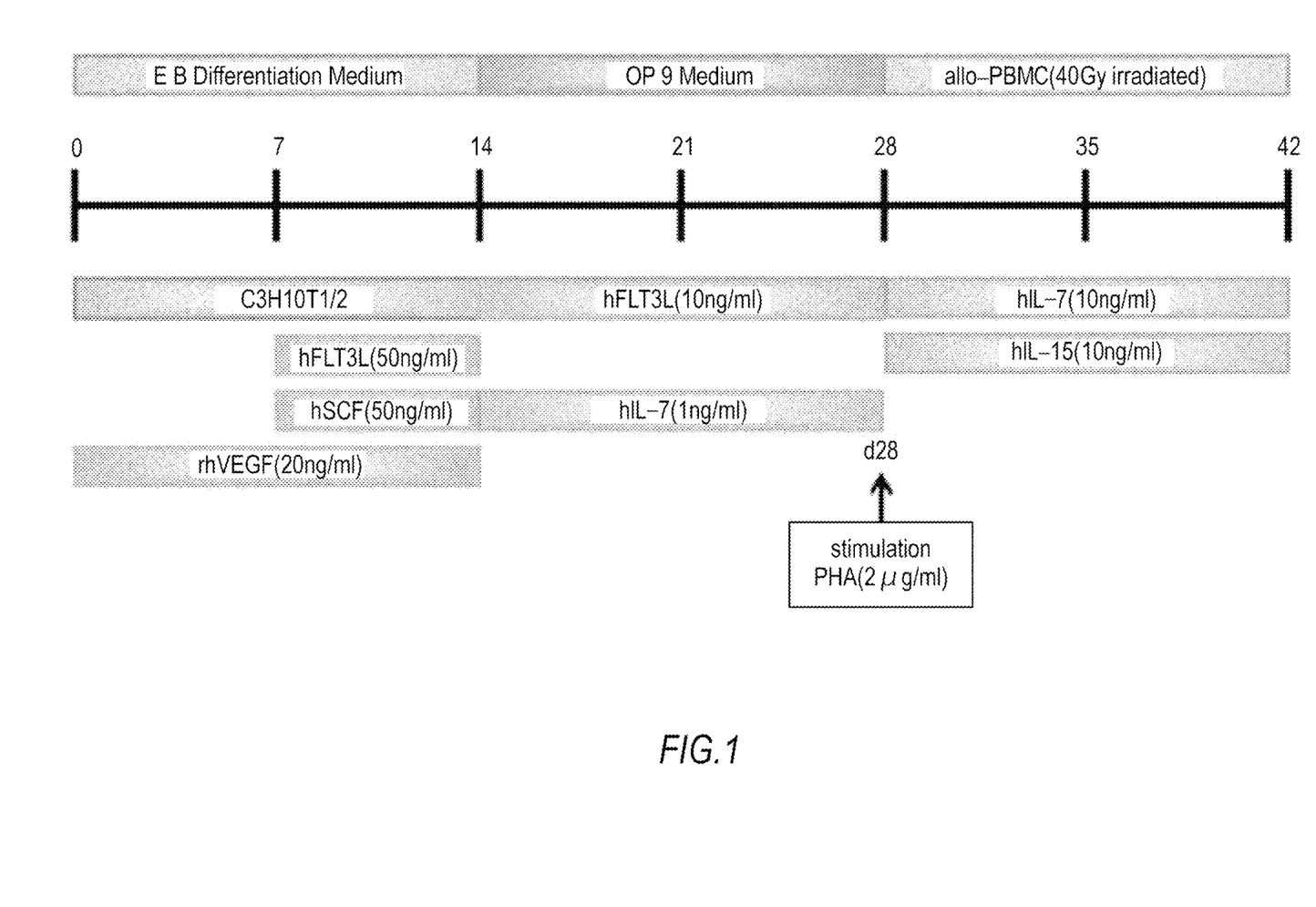
FIG. 1 shows a scheme illustrating induction of T cells from pluripotent stem cells.

Induction of differentiation of iPS cells into T cells was carried out according to Nishimura T, et al., Cell Stem Cell. 12(1):114-126, 2013. Details of the process were as follows (FIG. 1).

On confluent C3H10T1/2 cells in a 10-cm dish, a small cluster of iPS cells was plated (Day 0), and the cells were cultured for seven days under hypoxic conditions (5% $O_2$) in EB medium (IMDM supplemented with 15% fetal bovine serum (FBS), 10 μg/mL human insulin, 5.5 μg/mL human transferrin, 5 ng/mL sodium selenite, 2 mM L-glutamine, 0.45 mM α-monothioglycerol, and 50 μg/mL ascorbic acid) (Day 7).

Subsequently, 20 ng/mL VEGF, 30 ng/mL SCF, and 10 ng/mL FLT-3L (manufactured by Peprotech) were added, and culture was performed under normal oxygen pressure conditions for seven days (Day 14).

Hematopoietic cells contained in the resulting net-like structure (which is also referred to as iPS-SAC) (CD34+ hematopoietic stem/progenitor cells) were collected, and then plated on OP9-DL1 cells. The cells were then cultured in OP9 medium (αMEM supplemented with 15% FBS, 2 mM L-glutamine, 100 U/ml penicillin, 100 ng/ml streptomycin, 5.5 μg/mL human transferrin, and 5 ng/mL sodium selenite) supplemented with 10 ng/mL FLT-3L and 1 ng/mL IL-7, under normal oxygen pressure conditions for 14 days. Thereafter, 2 μg/ml phytohemagglutinin (PHA) was added thereto (Day 28). The cells were plated onto fresh OP9-DL1 cells every 3 to 4 days.

The obtained cells were mixed with allogeneic PBMCs irradiated with 40 Gy X-ray, and cultured in RH10 medium (RPMI-1640 supplemented with 10% human AB serum, 2 mM L-glutamine, 100 U/ml penicillin, and 100 ng/ml streptomycin) supplemented with 2 μg/ml PHA, 10 ng/ml IL-7, and 10 ng/ml IL-15 for 14 days to obtain T cells (b3a2-iPS-T cells) (Day 42).

For introduction of a CD4 gene into the obtained T cells, 2 μg/ml PHA was added to the obtained cells, and the CD4 gene was introduced using a retrovirus vector on Day 3 and Day 4 after the addition of PHA. The retrovirus vector was prepared by incorporating the CD4 gene into pDON-AI2 (Takara Bio Inc.).

Figure 2:
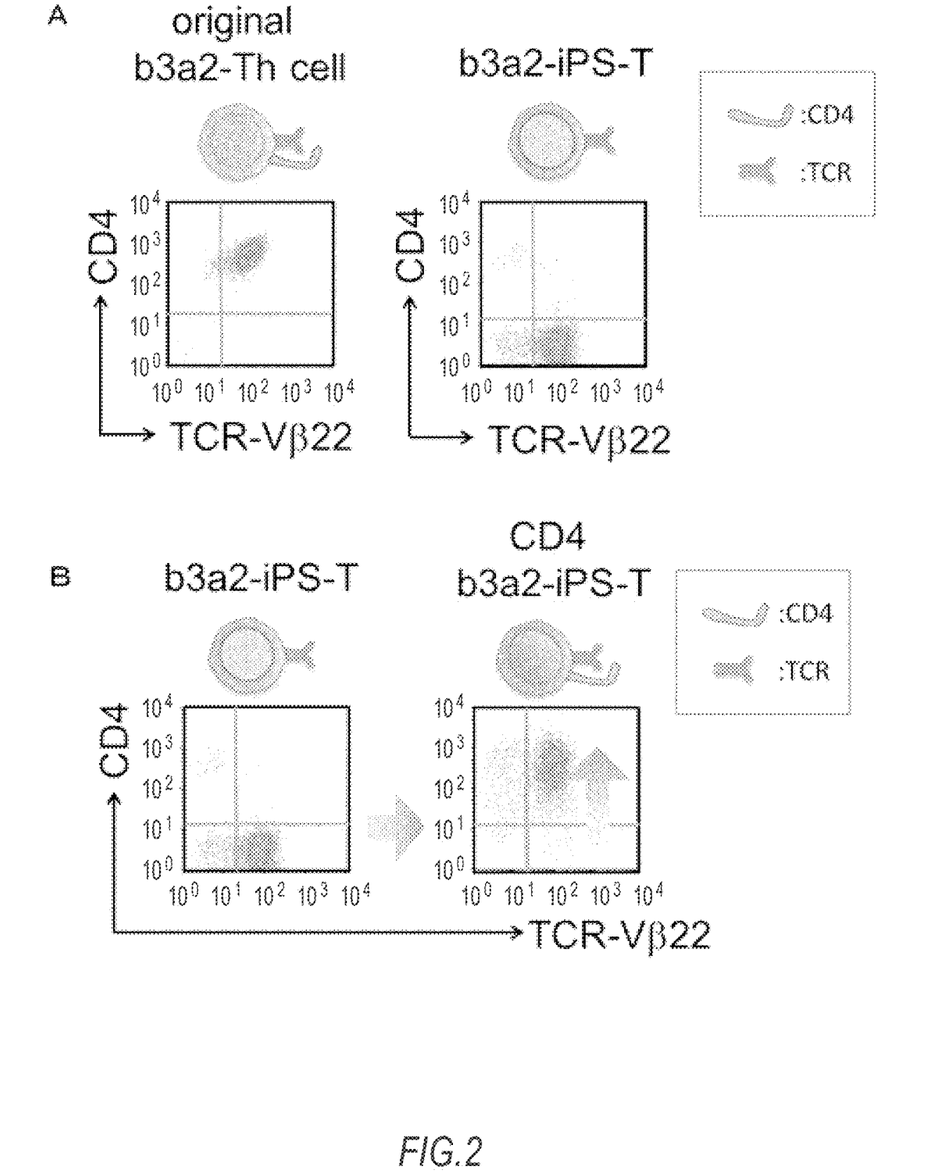
FIG. 2A shows the result of flow cytometry of collected Th cells (left column) and induced T cells (before introduction of a CD4 gene) (right column) using CD4 and TCR-Vβ22 as indices.
FIG. 2B shows the result of flow cytometry of induced T cells (before introduction of a CD4 gene) (left column) and induced T cells (after introduction of a CD4 gene) (right column) using CD4 and TCR-Vβ22 as indices.

The induced T cells having the CD4 gene introduced therein obtained by the method described above (CD4-b3a2-iPS-T cells) were subjected to measurement by a flow cytometer using an anti-TCR-Vβ22 antibody and an anti-CD4 antibody. As a result, TCR-Vβ22-positive CD4-positive cells were observed, which was similar to the collected human b3a2-Th cells (FIG. 2A and FIG. 2B). On the other hand, the b3a2-iPS-T cells without introduction of CD4 gene were found to be negative for CD4.

Figure 3:
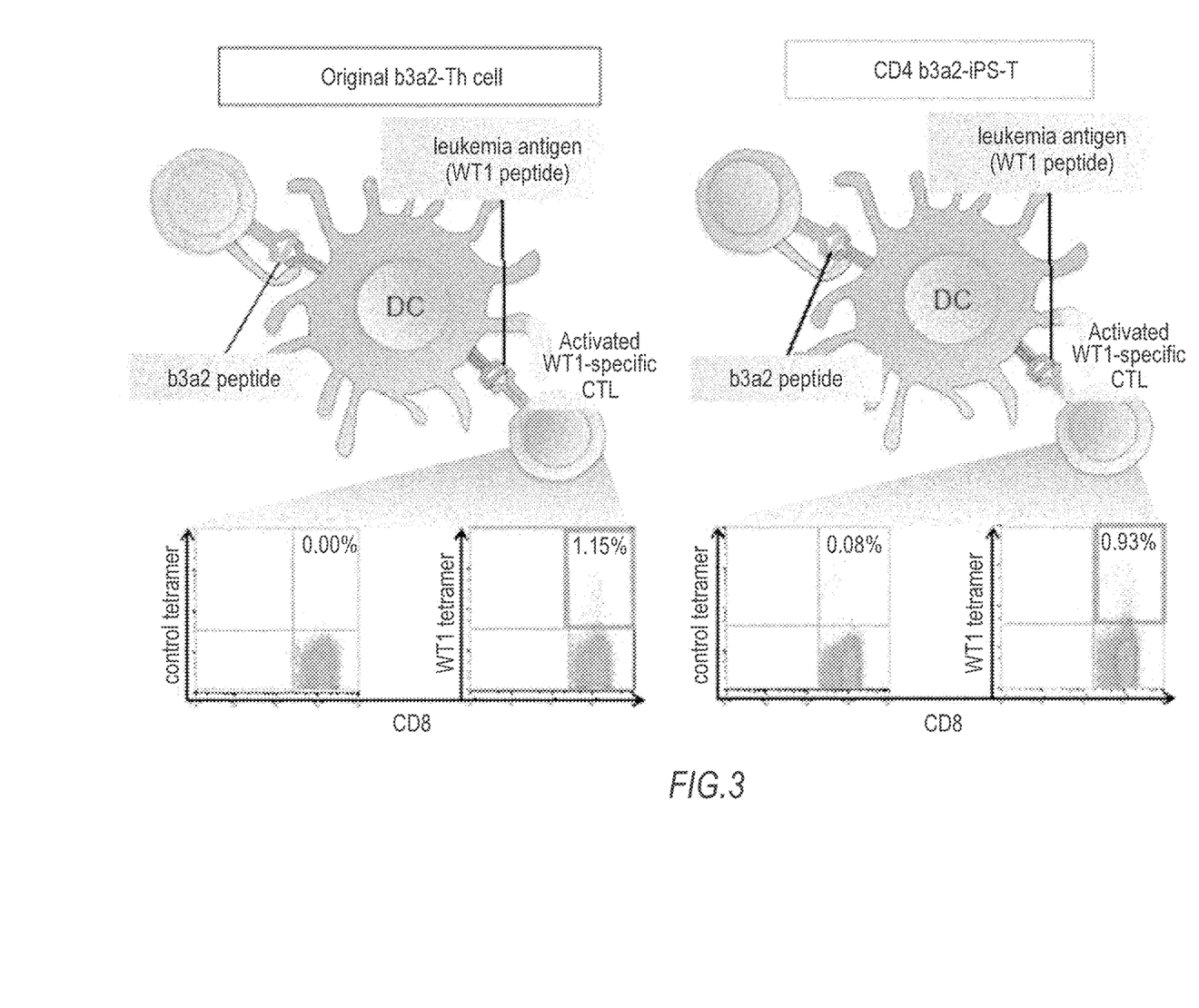
FIG. 3 shows the result of flow cytometry, using WT1 tetramer, of CD8-positive CTLs activated by DCs obtained by treatment with collected Th cells (left column) or induced T cells (after introduction of a CD4 gene) in the presence of an antigen (b3a2).

In RH10 medium supplemented with 10 μM b3a2 peptide (SEQ ID NO:1; ATGFKQSSKALQRPVAS), 1×10⁴ dendritic cells (DCs) and 5×10³ CD4-b3a2-iPS-T cells were co-cultured for 5 hours. The obtained cell culture was irradiated with 30 Gy X-ray to suppress the cell growth of the DCs and the CD4-b3a2-iPS-T cells. Subsequently, the WT1 peptide (SEQ ID NO:2; CYTWNQMNL) and 5×10⁴ CD8-positive T cells were added thereto, followed by performing culture for 1 week. The obtained cells were treated with an anti-CD8 antibody and WT1 tetramer, and analysis was carried out using a flow cytometer. As a result, the CD4-b3a2-iPS-T cells were found to have a capacity to induce antigen-specific CTLs through DCs specific to the b3a2 peptide, which was similar to the collected human b3a2-Th cells (FIG. 3).

Figure 4:
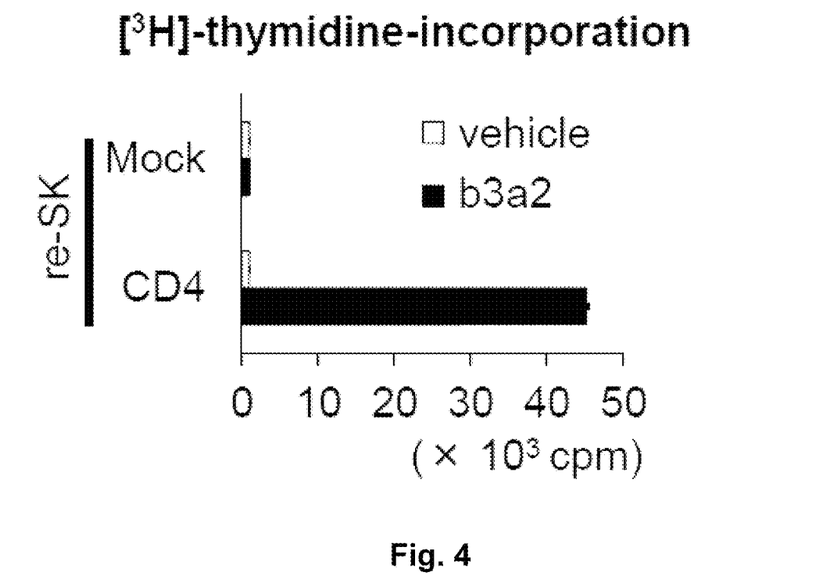
FIG. 4 shows the result of a [$^3$H]-thymidine incorporation assay for investigation of the growth abilities of b3a2-iPS-T cells (Mock) and CD4-b3a2-iPS-T cells (CD4).

For investigating the growth abilities of b3a2-iPS-T cells and CD4-b3a2-iPS-T cells, a [³H]-thymidine incorporation assay was carried out. The [³H]-thymidine incorporation assay was carried out according to the method of Bennett S R et al, J Exp Med. 1997; 186(1): 65-70. The results are shown in FIG. 4. It was shown that CD4-b3a2-iPS-T cells exhibit a good growth ability in response to antigen stimulation.

Figure 5:
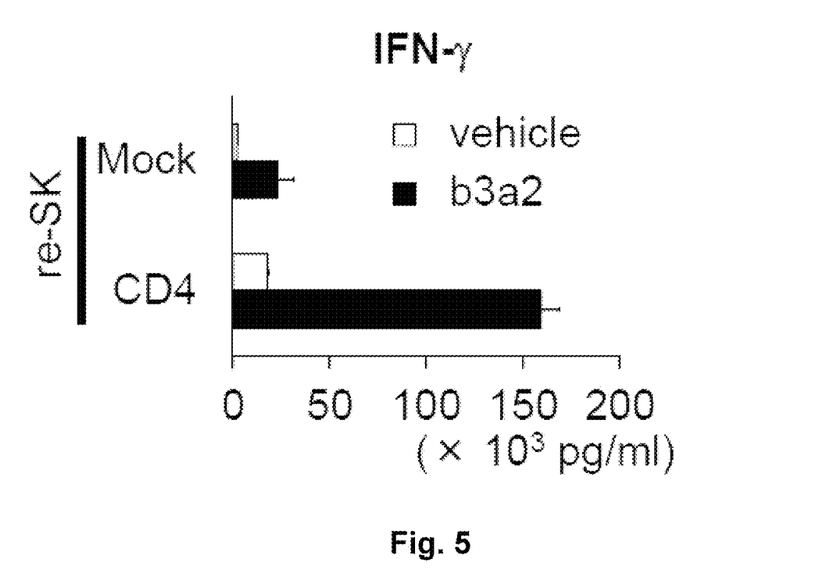
FIG. 5 shows the result of evaluation of the IFN-γ productivities of b3a2-iPS-T cells (Mock) and CD4-b3a2-iPS-T cells (CD4) by stimulation with dendritic cells preliminarily made to present 10 μM b3a2 peptide.

For evaluation of the IFN-γ productivity of the obtained CD4-b3a2-iPS-T cells, stimulation by dendritic cells preliminarily made to present 10 μM b3a2 peptide was carried out for the b3a2-iPS-T cells and the CD4-b3a2-iPS-T cells. Using the ELISA method (ELISA; hIFNγ: eBioscience) and the bead-based multiplex immunoassay (BD Cytometric Beads Array; BD Biosciences), the amount of IFN-γ released into the culture supernatant was measured for the b3a2-Th cells or the CD4-b3a2-iPS-T cells. The results are shown in FIG. 5. It was shown that the obtained CD4-b3a2-iPS-T cells have a very high IFN-γ productivity in response to antigen stimulation, as compared to the b3a2-iPS-T cells.

Thus, the forced expression of the CD4 gene in the T cells induced from pluripotent stem cells enabled induction of CD4-introduced iPS-derived T cells from CD4-positive Th cells specific to a tumor antigen of interest. The induced CD4-positive Th cells are expected to be capable of inducing an effective antigen-specific antitumor helper function, and considered to be an effective tool for development of a novel immune cell therapy.

What is claimed is:

1. An in vitro method for inducing CD4-positive T cells, the method comprising:
   (a) providing T-cells comprising a reconstituted T cell receptor (TCR) gene induced from an induced pluripotent stem cell, by a process comprising:
      (i) reprogramming a T helper cell comprising the TCR gene and recognizing an antigen in a culture medium to produce an induced pluripotent stem (iPS) cell comprising the reconstituted TCR gene;
      (ii) inducing CD34-positive hematopoietic progenitor cells from the pluripotent stem cells;
      (iii) culturing the CD34-positive hematopoietic progenitor cells of step (ii) in the presence of FLT3L and IL-7; and
      (iv) co-culturing the cells obtained from step (iii) with peripheral blood nuclear cells in presence of a mitogen, IL-7 and IL-15 to produce T cells comprising the reconstituted TCR gene, and
   (b) introducing a CD4 gene or a CD4 gene product into the T cells such that CD4-positive T cells comprising the reconstituted TCR gene are obtained,
      wherein the CD4-positive T-cells exhibit growth in response to the antigen stimulation, produce interferon-γ (IFN-γ) in response to the antigen stimulation, and activate dendritic cells (DCs), and wherein said induced pluripotent stem cells comprise the reconstituted TCR gene.

2. The method according to claim 1, wherein said Step (i) comprises co-culturing pluripotent stem cells with C3H10T1/2 cells, followed by co-culturing with C3H10T1/2 cells in the presence of VEGF, FLT3L, and SCF.

3. The method according to claim 1, wherein said Step (ii) comprises co-culturing said CD34-positive hematopoietic progenitor cells with stromal cells.

4. The method according to claim 3, wherein said stromal cells are OP9 cells expressing Delta-1.

5. The method according to claim 1, wherein introduction of the CD4 gene or the CD4 gene product is performed by retrovirus.

6. The method according to claim 1, wherein said pluripotent stem cells are human iPS cells.

7. The method according to claim 1, wherein said antigen is BCR/ABL.

8. An in vitro method for activating dendritic cells, said method comprising
   (a) providing T-cells comprising a reconstituted T cell receptor (TCR) gene induced from an induced pluripotent stem cell, by a process comprising:
      (i) reprogramming a T helper cell comprising the TCR gene and recognizing an antigen in a culture medium to produce an induced pluripotent stem (iPS) cell comprising the reconstituted TCR gene;
      (ii) inducing CD34-positive hematopoietic progenitor cells from the pluripotent stem cells;
      (iii) culturing the CD34-positive hematopoietic progenitor cells of step (ii) in the presence of FLT3L and IL-7; and
      (iv) co-culturing the cells obtained from step (iii) with peripheral blood nuclear cells in presence of a mitogen, IL-7 and IL-15 to produce T cells comprising the reconstituted TCR gene, and (b) introducing a CD4 gene or a CD4 gene product into the T cells such that CD4-positive T cells comprising the reconstituted TCR gene are obtained, and (c) co-culturing CD4-positive T cells comprising the reconstituted TCR gene obtained from step (b) with isolated dendritic cells in vitro in the presence of said antigen, wherein expression of the CD4 gene in the CD4-positive T-cells activate dendritic cells (DCs), exhibit growth in response to antigen stimulation, and produce interferon-γ (IFN-γ) in response to antigen stimulation, and wherein said induced pluripotent stem cells comprise the reconstituted TCR gene.

9. The method according to claim 8, wherein said antigen is a BCR/ABL fragment.

\* \* \* \* \*

SEQUENCE LISTING

<160> NUMBER OF SEQ ID NOS: 3

<210> SEQ ID NO 1

```
<211> LENGTH: 17
<212> TYPE: PRT
<213> ORGANISM: Artificial Sequence
<220> FEATURE:
<223> OTHER INFORMATION: b3a2

<400> SEQUENCE: 1

Ala Thr Gly Phe Lys Gln Ser Ser Lys Ala Leu Gln Arg Pro Val Ala
1               5                   10                  15

Ser

<210> SEQ ID NO 2
<211> LENGTH: 9
<212> TYPE: PRT
<213> ORGANISM: Artificial Sequence
<220> FEATURE:
<223> OTHER INFORMATION: WT1

<400> SEQUENCE: 2

Cys Tyr Thr Trp Asn Gln Met Asn Leu
1               5

<210> SEQ ID NO 3
<211> LENGTH: 458
<212> TYPE: PRT
<213> ORGANISM: Homo sapiens

<400> SEQUENCE: 3

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
                20                  25                  30

Lys Gly Asp Thr Val Glu Leu Thr Cys Thr Ala Ser Gln Lys Lys Ser
            35                  40                  45

Ile Gln Phe His Trp Lys Asn Ser Asn Gln Ile Lys Ile Leu Gly Asn
        50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
                100                 105                 110

Asp Gln Lys Glu Glu Val Gln Leu Leu Val Phe Gly Leu Thr Ala Asn
            115                 120                 125

Ser Asp Thr His Leu Leu Gln Gly Gln Ser Leu Thr Leu Thr Leu Glu
        130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
            195                 200                 205

Ser Ile Val Tyr Lys Lys Glu Gly Glu Gln Val Glu Phe Ser Phe Pro
        210                 215                 220

Leu Ala Phe Thr Val Glu Lys Leu Thr Gly Ser Gly Glu Leu Trp Trp
225                 230                 235                 240
```

```
Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
                260                 265                 270

Gln Met Gly Lys Lys Leu Pro Leu His Leu Thr Leu Pro Gln Ala Leu
                275                 280                 285

Pro Gln Tyr Ala Gly Ser Gly Asn Leu Thr Leu Ala Leu Glu Ala Lys
                290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
                340                 345                 350

Lys Arg Glu Lys Ala Val Trp Val Leu Asn Pro Glu Ala Gly Met Trp
                355                 360                 365

Gln Cys Leu Leu Ser Asp Ser Gly Gln Val Leu Leu Glu Ser Asn Ile
                370                 375                 380

Lys Val Leu Pro Thr Trp Ser Thr Pro Val Gln Pro Met Ala Leu Ile
385                 390                 395                 400

Val Leu Gly Gly Val Ala Gly Leu Leu Leu Phe Ile Gly Leu Gly Ile
                405                 410                 415

Phe Phe Cys Val Arg Cys Arg His Arg Arg Arg Gln Ala Glu Arg Met
                420                 425                 430

Ser Gln Ile Lys Arg Leu Leu Ser Glu Lys Lys Thr Cys Gln Cys Pro
                435                 440                 445

His Arg Phe Gln Lys Thr Cys Ser Pro Ile
450                 455
```